United States Patent [19]

Werner et al.

[11] Patent Number: 4,502,782
[45] Date of Patent: Mar. 5, 1985

[54] METHOD AND LASER APPARATUS FOR MEASURING VISUAL RANGE, SLANT VISUAL RANGE AND CLOUD ALTITUDE

[75] Inventors: Christian Werner, Munich; Michael Klier, Puchheim, both of Fed. Rep. of Germany

[73] Assignee: Deutsche Forschungs- und Versuchsanstalt für Luft- und Raumfahrt e.V., Linder Höhe, Cologne, Fed. Rep. of Germany

[21] Appl. No.: 226,470

[22] Filed: Jan. 19, 1981

[30] Foreign Application Priority Data

Jan. 26, 1980 [DE] Fed. Rep. of Germany ....... 3002791

[51] Int. Cl.³ .................... G01C 3/08; G01N 21/00
[52] U.S. Cl. .............................. 356/5; 356/342
[58] Field of Search ........................... 356/5, 342

[56] References Cited

U.S. PATENT DOCUMENTS

| | | |
|---|---|---|
| 3,510,225 | 5/1970 | Collis .................... 356/342 |
| 3,519,354 | 7/1970 | Brown, Jr. et al. ............ 356/342 |
| 3,782,824 | 1/1974 | Stoliar et al. ............... 356/342 |

OTHER PUBLICATIONS

"Lidar Für Umweltschutzaufgaben", Deutsche Forschungs-und Versuchsanstact Für Luft–und Raumfahrt e.V. Institut Für Physik Der Atmosphare, Jul. 4, 1979.
C. Werner, Optics & Laser Technology, Feb. 1981, vol. 13, No. 1, 356-5.

Primary Examiner—S. C. Buczinski
Attorney, Agent, or Firm—Frishauf, Holtz, Goodman & Woodward

[57] ABSTRACT

A laser echoe ranging device (lidar) is used both to measure cloud height and to measure slant range visibility. For the latter purpose at various elevation angles, the distance for which the echoe gets down to the noise level is measured by a counter and the echo voltage for a distance selected by a time switch is also stored, for example for various distances in 100 meter steps. These values can be used to compute the slant visual range and, with reference to the data for the different angles of elevation, also the layer structure of an inhomogeneous scattering characteristic of the atmosphere.

1 Claim, 7 Drawing Figures

METHOD AND LASER APPARATUS FOR MEASURING VISUAL RANGE, SLANT VISUAL RANGE AND CLOUD ALTITUDE

This invention concerns measurement of the horizontal and slant range of visibility, the altitude of clouds and the distance of fog banks by means of a pulsed laser transmitter and a receiver using a photodetector.

With the constantly increasing density of traffic on land and in the air and the ever-increasing velocities of travel, it is often a matter of life and death to know with precision the prevailing conditions of visibility. Fog warnings on motor vehicle expressways are an example. At places at which fog is known to form readily, visibility measuring instruments can be permanently installed, which can control the flow of traffic in accordance with the range of visibility, for example by controlling illuminated warnings setting specific speed limits.

Air traffic is continually subject to the disadvantage that fog at the airport makes take-offs and landings difficult or impossible. In this situation, it is particularly important to know and to predict the visibility conditions prevaling on the runways used for take-offs and landings. Technical facilities for that purpose, up to now, are usually transmission measuring devices and light density measurers on the ground by the help of which the so-called runway visual range (RVR) is determined. In addition, the visibility along the landing glide path should actually be monitored and the so-called slant visual range (SVR) determined.

FIG. 1 sets forth the geometric relations in the case of aircraft landing. An aircraft of an arriving flight located on the glide path successively passes in flight the horizontal visibility stages $V_N$, $V_{N1}$ and $V_{N2}$. From the airport, only the horizontal visibility in the layer $V_{N2}$ immediately above the runway can be announced to the pilots, this visibility being measured with a transmission meter operating between the points $T_1$ and $T_2$. For the pilots who are responsible for safe landing, however, it is in every case more important to know the visibility along the glide path.

In an arrival through clouds (e.g. $V_{N1} < V_{No}$ and $V_{N1} < V_{N2}$) the height of the lower boundary of the clouds and the thickness of the cloud layer is of interest. The determination of the first of these is carried out with ceilometers or clouds height measurers. For the case of ground fog ($V_{N2} < V_{N1}$ or $V_{No}$), the height of the upper boundary of the fog and the optical homogeniety needs to be known, and in such situations it is unusually difficult for the responsible persons to provide precise information as to whether the arriving pilot can count on runway visibility at the critical point indicated in FIG. 1, whether he must be prepared to abort the landing approach or whether the visibility conditions do not permit a safe landing at all, using supplementary information, for example from balloon ascensions or appropriate experience. In critical weather conditions of that kind, which unfortunately are not rare, a continuous instrumental monitoring of the slant range visibility would be of great advantage.

The visual range, besides being determinable with transmission meters, can be determined with devices that measure only the scattering coefficient. For the determination of normal slant visibility range, transmission meter paths can be plotted theoretically on the glide path. The towers that would be necessary in the landing region for that purpose, would in any event provide sources of danger. The installation of remote sensing devices and particularly laser, radar, or lidar devices thus appears appropriate.

In this manner of proceeding, the energy backscattered by the aerosol particles shows a characteristic relation from the roundtrip time of the laser pulse. In the received signal, the properties of the aerosols, as for example their density, along the laser beam are characterized. If by way of simplification a homogeneous atmosphere along the path is assumed, which would be connected with a constant backscattering on the corresponding path lengths, the curve portion of the lidar signal is determined by the product of the reciprocal of the square of the distance and the extinction. Because of the known relation of the visual range to the extinction, the visual range along the laser beam can be obtained by exact analysis of the lidar signal. The advantage of the remote sensing technology is the independence of any measuring installation. It is possible to measure even along the broken line shown in FIG. 1 (slant visual range).

The most precise evaluation method heretofore known, the so-called slope method (Applied Optics 14 (1975), p. 2878–2882) requires a great expense for the necessary electronics for signal storage and the computational determination of the straight lines of symmetry out of the distance-corrected signal data. From that, the inclination is obtained for the curve that directly yields the extinction. The practical introduction of the method runs up against the necessary high cost of personnel and equipment.

Another procedure, that solves the cost problems, provides unambiguous results only with a supplementary independent visibility measurement. The so-called maximum detectable range method (described in DE-PS No. 26 06 318) utilizes, as the criterion, the limit of detectability of the back-scattered signal. This maximum detectable range of the signal can be the same for the case of good visibility, thus with small aerosol content and thereby small backscattering, and in the case of fog, in which this maximum detectable range is obtained through the stronger extinction. The determination can then be performed only with another independent measurement of visibility. In particular, this known method is limited to visibility ranges under 1.4 km.

THE INVENTION

It is an object of the present invention to provide a simplified method for determining the slant visual range and a laser measuring apparatus for carrying out this method requiring relatively small expense for electronic equipment.

Briefly, for determining the maximum detectable range of the laser beam, a second point at a distance less than 200 meters from the laser transmitter is used for which measurements are stored and measurements are made at various angles of elevation.

A laser range finder is used, preferably one equipped with a circuit for storing a voltage that contains a rapid analog-to-digital converter, to the output of which the input of a memory is connected.

A second support or reference point of the lidar signal is required which furnishes measurement value that provides data regarding the magnitude of the backscattering in the immediate neighborhood of the receiver. The electronics expense for the storing of a voltage value and its computation in connection with the maximum detectable range of the signal is small compared to the expensive slope method. The possible remaining disadvantage that inhomogeneities in the course of the signal between the first and second support points may lead to erroneous interpretations is excluded according to the invention by measuring again at another elevation angle.

BRIEF DESCRIPTION OF THE DRAWINGS

The invention is further described by way of examples with reference to the annexed drawings, in which.

By way of introduction to the detailed description that follows, it should be mentioned that whereas the heretofore known solutions of the problem for determining the normal slant visual range from a lidar signal are either connected with great expense for electronics or else provide unambiguous results only in connection with a further visibility observation. In the method according to the invention, an effort is made toward the goal of reducing the expense of the exact solution method known as the slope method. For homogeneous air layers, it is possible to obtain the desired results with two reference or support points. The second support point serves the purpose of giving information regarding the magnitude of backscattering in the immediate neighborhood of the receiver, for example the signal voltage $U_B$ when R equals $R_B$ at 100 meters. In practice, the arbitrary value $U = U_R$ can be so chosen that it is independent of amplifier facilities that are possibly present. This is obtained if it is assumed that for $U = U_R$, the signal-to-noise ratio is 1, which means that the signal then vanishes into the receiver noise.

In what follows, the precision limits of the two-point method are explained also for inhomogeneous layers of the real atmosphere.

Figure 1:
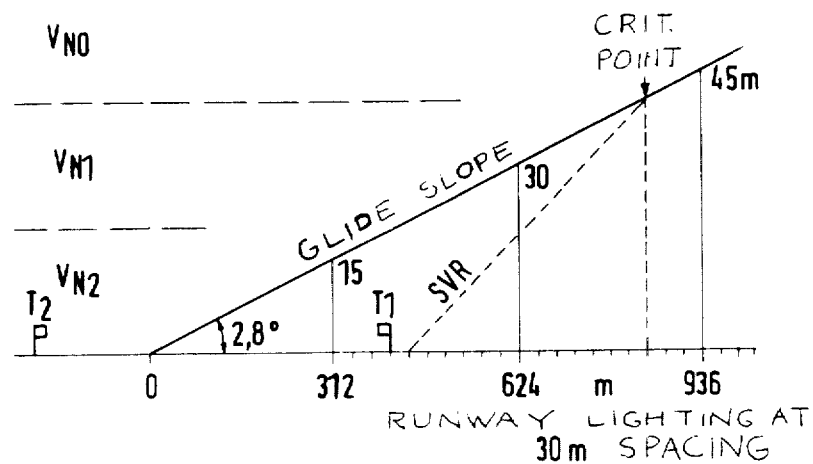
FIG. 1 is a graph for explaining the conditions of an aircraft landing path.
Figure 2A:
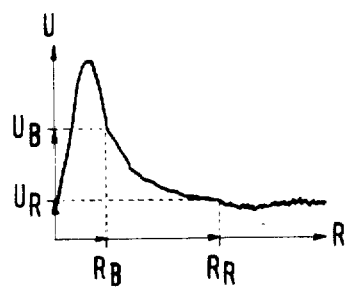
FIGS. 2a and 2b are graphs to the same range scale respectively relating to a linearly amplified signal and to a logarithmically amplified signal.

For illustrating the two-point method, FIG. 2a shows a signal such as is obtained when using linear amplification with each laser pulse. $1/R^2$ dependency is clearly to be recognized. In a manner analogous to the slope method, two points can be selected out with the result set forth below by use of the following equations:

$$U_R = A = \frac{K}{R_R^2} \cdot \beta_{MR} \tau_R^2$$

$$U_B = B = \frac{K}{E_B^2} \cdot \beta_{MB} \tau_B^2$$

under the assumption that $$\beta_{MR} = \beta_{MB} = \bar{\beta}$$

homogeneous layers

-continued
$$\sigma_{MR} = \sigma_{MB} = \bar{\sigma}$$

Results obtained:

$$\frac{AR_R^2}{BR_B^2} = e^{-2\bar{\sigma}(R_R - R_B)}$$

$$\bar{\sigma} = \frac{1}{2(R_R - R_B)} \cdot \ln \frac{BR_B^2}{AR_R^2}$$

$$V_N = \frac{7.82 \cdot (R_R - R_B)}{\ln BR_B^2 - \ln AR_R^2}$$

In the above considerations, four measured values are involved, the measured voltage $U_B$ at the distance $R_B$ and the measured voltage $U_R$ at the distance $R_R$.

If now the effective range method is utilized with $U_R$ as the noise voltage value, then there are only two measurement magnitudes yet to be determined: the measured voltage $U_B$ at the fixed distance $R_B$ and the noise distance $R_R$ for a known noise voltage $U_R$. This noise voltage value is the only difference from the slope method, where any voltage value whatever is taken at the distance R. The measurement problem remains the measurement of the distance $R_R$. For this purpose, a logarithmic amplifier converted into a gate circuit is useful.

Figure 2B:
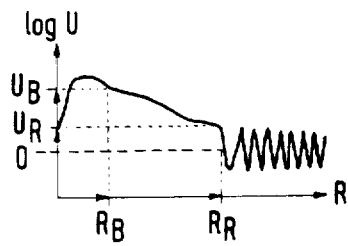

FIG. 2b shows the logarithmically amplified signal. As a result of the same amplification for positive as for as negative voltages, when the noise voltage is reached, a null passage results for the logarithmically amplified signal. The measurement of the noise range is thus reduced to a start-stop count such as is known for distance measurements.

Calculated layer structure models show the limits of the effective range method. With an additional measurement at right angles, misinterpretations can be excluded.

DESCRIPTION OF PREFERRED EMBODIMENTS

Figure 3:
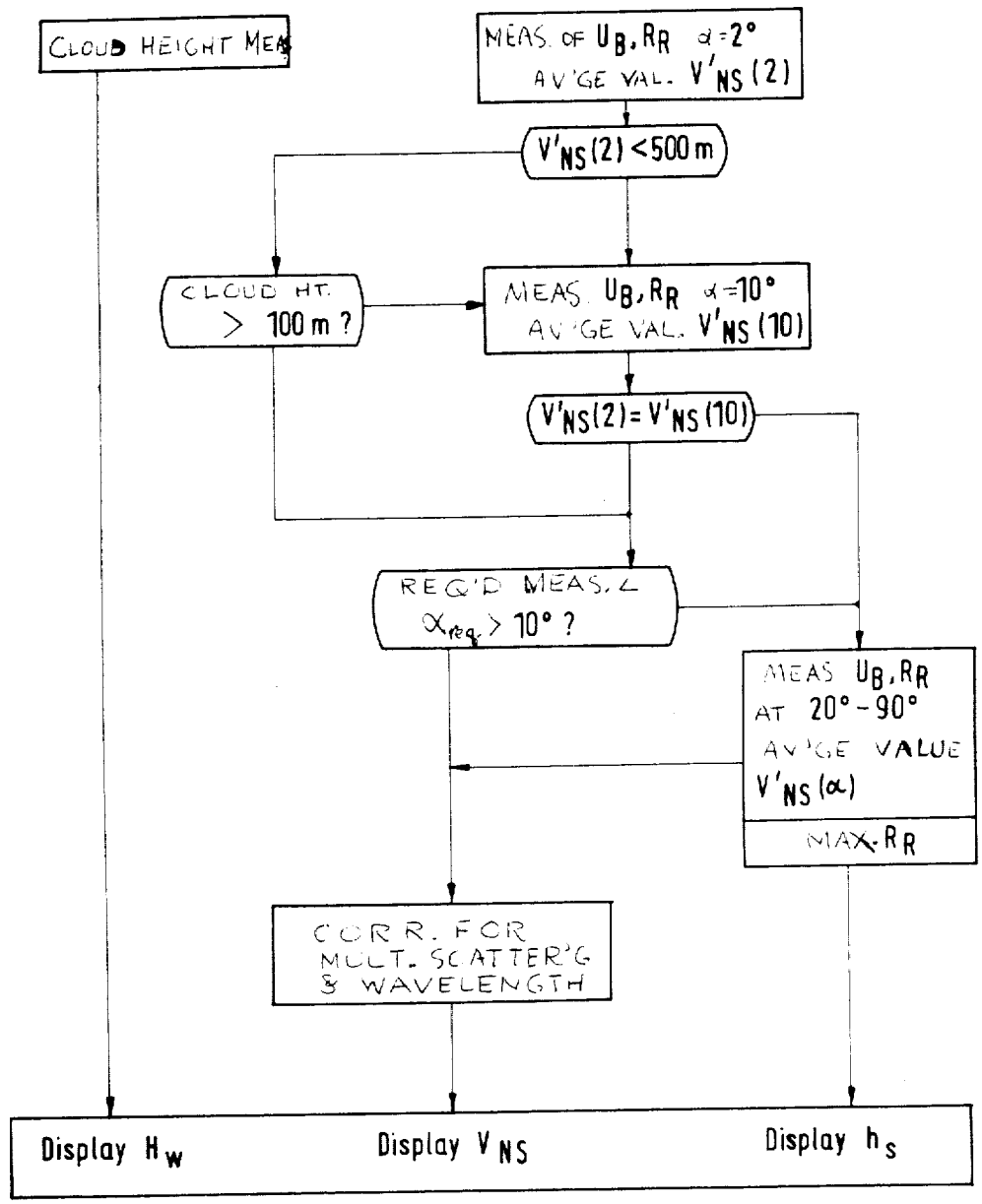
FIG. 3 is a logic flow diagram for explanation of the method of the invention.

FIG. 3 shows a preferred illustrative example of a logic flow plan.

In the normal case, the measurement is carried out at two angles, the measured values are obtained and a visual range $V_2$ and a visual range $V_{10}$ are determined, after which both values are compared. If a layer structure is not involved, a value $V_x$ with the corresponding conversion factors (multiple scattering, wavelengths) is adequate for display. If a layer structure is to be indicated, $V_2$ must be different from $V_{10}$, and further measurements up to 90° are carried out in order to determine a maximum of $R_R$ for indicating the inversion height as well as the corrected visual range value at the angle of interest. The provision of the true slant visual range for the pilot then depends upon the path radiance.

For measuring cloud height and slant visual range, a small Nd-glass lidar serves as a suitable apparatus, for example with the following specifications:

| Laser: | |
|---|---|
| Nd-glass laser | 1.064 μm (made by Zeiss) |
| Output power | 3 megawatts |
| Output energy | 150 milli Joule |
| Pulse length | 20 ns |
| Maximum repetition rate | 1 Hz |
| Receiver: | |

| | |
|---|---|
| Mirror diameter | 13.4 cm |
| Detector | YAG 444 photodiodes |
| Logarithmic amplifier | device made by American Astrionics |

The term "lidar", like "radar", is an acronym. In this case, it signifies a laser indicator of distance and range.

Figure 4:
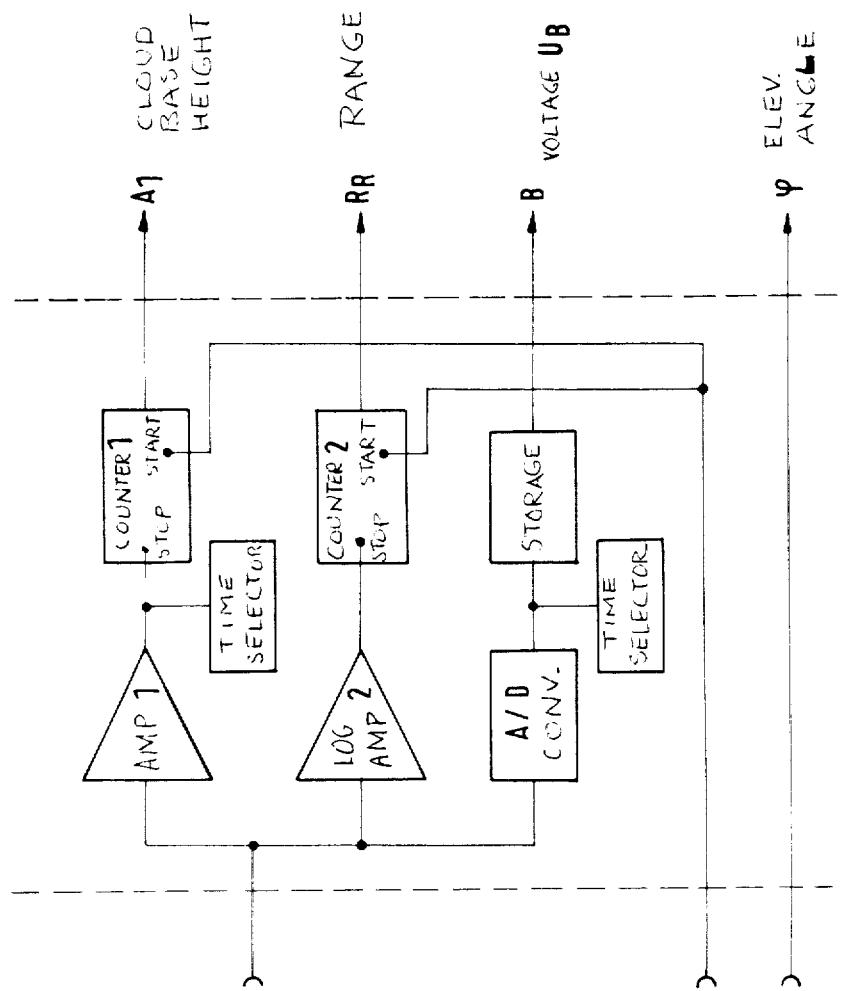
FIG. 4 is a block circuit diagram of the signal processing in the apparatus of the invention.

FIG. 4 shows the block circuit diagram for the signal processing. The lidar signal can be used for cloud height measuring with known types of distance measuring circuits. The start signal is delivered by the laser trigger and the stop signal by the cloud echo. By means of a time switch, it is possible to measure the height of the second or third cloud layer, as well as the first.

For the slant visual range measurement, the same distance measuring is performed with the stop signal as the signal for passage through zero. In addition, a value of the lidar signal is stored for the selectable distance $R_B$ which is selected by means of a time switch. According the mode of operation, either the values of cloud height or the values $R_R$ and $U_B$ are provided to the computer. In addition, information is made available to indicate the measuring angle.

Figure 5:
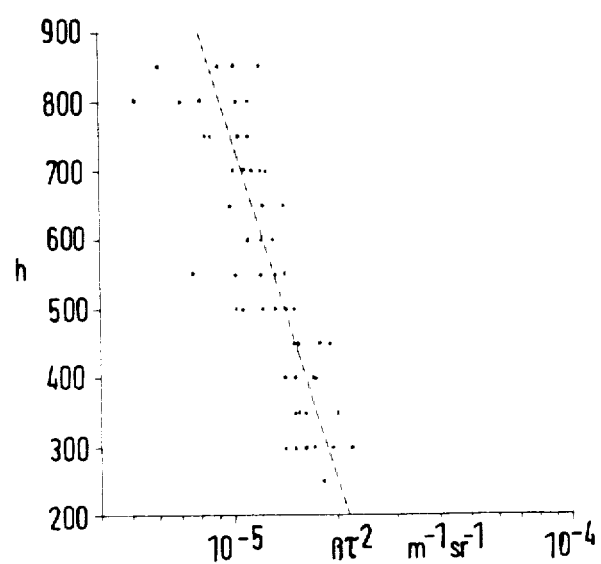
FIG. 5 is a graphical representation of measurement results.

FIG. 5 shows the vertical course of the result values of $\beta\tau^2$ obtained in an experiment. If homogeneous distribution is assumed, the slope function can be determined from the illustrated mean curve and following visual range is obtained:

$$V_{slope} = 5.4 \text{ km.}$$

The effective range method gave the following values for $R_R$: 925, 948, 1063, 894, 897, 975, 942, 960, 933, 960 m.

With the obtained initial values $R_B = 250$ m, $U_B = 0.17$ V and $U_R = 0.005$ V and the mean effective range $R_R = 950$ m, there is obtained a visual range of 5.9 km. Since there is present no information regarding the course of the value $\beta\tau^2$ in the lowermost 250 m, the small deviation is possibly due to the deviations of the experimental points from the broken line shown in FIG. 5.

Figure 6:
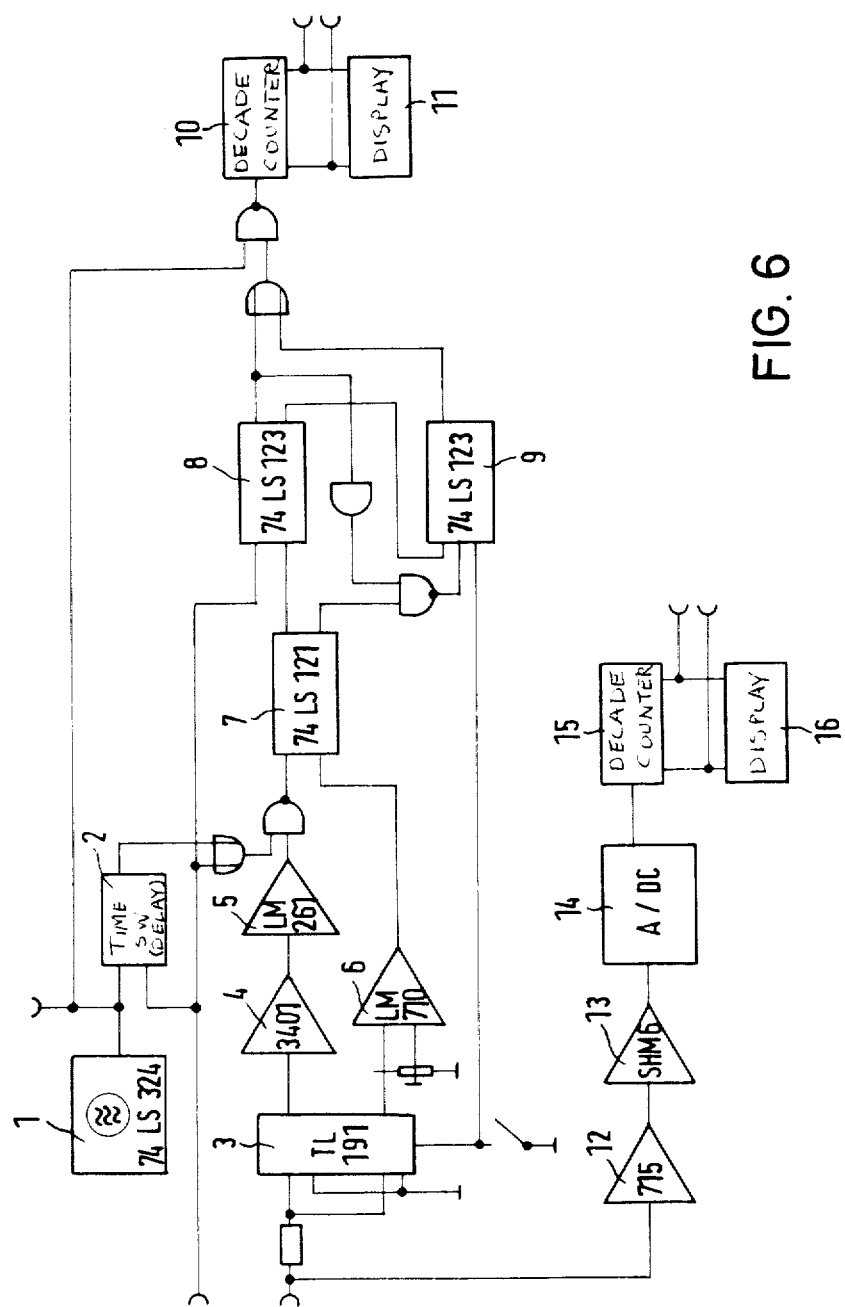
FIG. 6 is a circuit diagram, mainly in block form, for a measuring apparatus for carrying out the method of the present invention.

The circuit diagram shown in FIG. 6 concerns a measuring apparatus for carrying out the method of the invention. The circuit contains an oscillator 1, which is necessary for producing the counting frequency for determination of the cloud height, the slant visual range and the distance. A time switch 2 is connected to the oscillator 1, particularly to make possible the measurement of second or third echoes and for storing the measurement value corresponding to the time or period met by the switch.

An amplifier for the signal preparation of the laser beam for determining the effective range $R_R$ contains an electronic switch 3, an amplifier circuit 4,5 and a comparator circuit 6. By means of a flipflop circuit 7, an analog signal is converted into a digital signal, which is supplied to flipflop circuits 8 and 9 to which a decade counter 10 is connected for controlling an optical indicator 11. Two other amplifier units 12 and 13 are connected to the signal input for measuring the voltage $U_B$, and the output of the latter of them is connected to an analog-to-digital converter 14, to which likewise a decade counter 15 having an indicating device 16 is connected.

Upon the initiation of a laser pulse, a trigger pulse is first produced that resets the condition of all counters to zero. At the same time, the start pulse is generated for the counter. The echo that reaches the signal input is amplified by the amplifiers 4,5. Digitalization takes place in the flipflop circuits 7,9 and the output signal is supplied to the decade counter 10. In the comparator 6, the stop signal is generated when the signal voltage goes below the voltage $U_R$. Then it is possible to read off the measured value of the effective range $R_R$ at the indicating device 11. At the same time, at the indicating device 16, the value $U_B$ is indicated, e.g. the signal voltage $U_B$ at the range $R = R_B$ of 100 m.

The two measured values $U_B$ and $R_R$ are supplied along with the laser beam angle data over an IEEE 488 bus to the computer for such further processing as may be desired.

Although the invention has been described with reference to a particular illustrative example, it will be understood that variations and modifications are possible within the inventive concept.

Reference to related publications: Gazzi et al AGARD—CP—183 (1976)

We claim:

1. Method of measuring visibility range, slant visibility range and cloud height for air navigation assistance by use of a pulse transmitter and a photo-detector-equipped receiver for receiving laser pulses back-scattered by an aerosol, in which a signal voltage ($U_R$) dependent on the properties of said aerosol and the range ($R_R$) of the backscattering aerosol determined from the propogation time of the laser pulses between transmission and reception are measured for a first reference point and in which a voltage ($U_B$) of received laser pulses and a corresponding range ($R_B$) is measured for a second reference point in the neighborhood of the transmitter for determination of the maximum range measurable with the laser transmitter, and the measurements for said first and second reference points are stored in a computer for further evaluation, said method also including the improvement whereby additional measurements are made at different elevation angles in order to detect atmospheric layering and, in the event of detection of layering, to furnish results relating thereto to said computer for correction of slant visibility range computation.

* * * * *